United States Patent
Witte et al.

(10) Patent No.: US 7,816,347 B2
(45) Date of Patent: Oct. 19, 2010

(54) PHARMACEUTICAL COMPOSITIONS COMPRISING NEP-INHIBITORS, INHIBITORS OF THE ENDOGENOUS ENDOTHELIN PRODUCING SYSTEM AND HMG COA REDUCTASE INHIBITORS

(75) Inventors: Klaus Witte, Hannover (DE); Dieter Ziegler, Hemmingen (DE); Matthias Straub, JW Groet (NL); Paulus Antonius Remigius Koopman, VL Amstelveen (NL)

(73) Assignee: Solvay Pharmaceuticals GmbH, Hannover (DE)

( * ) Notice: Subject to any disclaimer, the term of this patent is extended or adjusted under 35 U.S.C. 154(b) by 1105 days.

(21) Appl. No.: 11/302,512

(22) Filed: Dec. 14, 2005

(65) Prior Publication Data

US 2006/0189595 A1    Aug. 24, 2006

Related U.S. Application Data

(60) Provisional application No. 60/635,963, filed on Dec. 15, 2004.

(51) Int. Cl.
   A61K 31/55    (2006.01)
   A61K 31/401   (2006.01)
   A61K 31/366   (2006.01)
   A61K 31/22    (2006.01)
   A61P 9/12     (2006.01)

(52) U.S. Cl. .................. 514/212.07; 514/423; 514/460; 514/548

(58) Field of Classification Search .............. 514/7, 514/212.07, 423, 460, 548
   See application file for complete search history.

(56) References Cited

U.S. PATENT DOCUMENTS

| | | | |
|---|---|---|---|
| 4,049,495 A | 9/1977 | Endo et al. | |
| 4,231,938 A | 11/1980 | Monaghan et al. | |
| 4,346,227 A | 8/1982 | Terahara et al. | |
| 4,444,784 A | 4/1984 | Hoffman et al. | |
| 4,681,893 A | 7/1987 | Roth | |
| 4,739,073 A | 4/1988 | Kathawala | |
| 4,749,688 A | 6/1988 | Haslanger et al. | |
| 4,925,852 A | 5/1990 | Kesseler et al. | |
| 5,006,530 A | 4/1991 | Angerbauer et al. | |
| 5,011,930 A | 4/1991 | Fujikawa et al. | |
| 5,082,859 A | 1/1992 | Festal et al. | |
| 5,134,157 A | 7/1992 | Laruelle et al. | |
| 5,260,440 A | 11/1993 | Hirai et al. | |
| 5,677,297 A | 10/1997 | Waldeck et al. | |
| 5,681,966 A * | 10/1997 | Cai et al. | 549/65 |
| 5,783,573 A | 7/1998 | Rozsa et al. | |
| 5,952,327 A | 9/1999 | Waldeck et al. | |
| 6,028,075 A | 2/2000 | Pines et al. | |
| 6,455,574 B1 | 9/2002 | Buch | |
| 6,482,820 B2 | 11/2002 | Wilkins et al. | |
| 6,777,443 B2 | 8/2004 | Fink | |
| 7,045,653 B2 * | 5/2006 | Dack et al. | 562/450 |
| 2002/0049237 A1 | 4/2002 | Newton et al. | |
| 2002/0183260 A1 | 12/2002 | Fink | |
| 2003/0008904 A1 | 1/2003 | Buch | |
| 2003/0040512 A1 | 2/2003 | Rozsa et al. | |
| 2004/0048906 A1 | 3/2004 | Buch et al. | |
| 2004/0092573 A1 | 5/2004 | Robl et al. | |
| 2004/0162345 A1 | 8/2004 | Berger et al. | |
| 2004/0176393 A1 | 9/2004 | Newton et al. | |
| 2004/0192584 A1 | 9/2004 | McMahon et al. | |
| 2004/0235754 A1 | 11/2004 | Fink | |
| 2004/0266698 A1 | 12/2004 | Fink | |
| 2005/0020607 A1 | 1/2005 | Newton et al. | |
| 2005/0038012 A1 | 2/2005 | Eerden et al. | |

FOREIGN PATENT DOCUMENTS

| | | |
|---|---|---|
| EP | 0 254 032 A2 | 1/1988 |
| EP | 0 733 642 A1 | 9/1996 |
| EP | 0 830 863 A1 | 3/1998 |
| EP | 0 916 679 A1 | 5/1999 |
| WO | WO 99/11259 A1 | 3/1999 |
| WO | WO 99/47138 A1 | 9/1999 |
| WO | WO 00/48601 A1 | 8/2000 |
| WO | WO 01/03699 A1 | 1/2001 |
| WO | WO 02/092622 A2 | 11/2002 |
| WO | WO 02/094176 A2 | 11/2002 |
| WO | WO 03/027091 A1 | 4/2003 |

(Continued)

OTHER PUBLICATIONS

Dessi Fulgheri et al. "The natriuretic peptide system in obesity-related hypertension: new pathophysiological aspects", Journal of Nephrology, vol. 11, No. 6, 1998, pp. 296-299.

(Continued)

*Primary Examiner*—Shengjun Wang
*Assistant Examiner*—Sahar Javanmard
(74) *Attorney, Agent, or Firm*—Crowell & Moring LLP

(57) ABSTRACT

A combination therapy is disclosed for treating or inhibiting cardiovascular or metabolic diseases or conditions through a combination of at least one inhibitor of neutral endopeptidase (=NEP), at least one inhibitor of the endogenous endothelin producing system and at least one HMG CoA reductase inhibitor. Pharmaceutical compositions are also described comprising NEP inhibitors, inhibitors of the endogenous endothelin producing system and HMG CoA reductase inhibitors and the use of these pharmaceutical composition in the prophylaxis or treatment of cardiovascular and/or metabolic disorders or diseases in mammals (including humans).

13 Claims, No Drawings

FOREIGN PATENT DOCUMENTS

| WO | WO 03/059939 A1 | 7/2003 |
| WO | WO 2004/082636 A2 | 9/2004 |
| WO | WO 2005/030795 A1 | 4/2005 |

OTHER PUBLICATIONS

Tabrizchi, "SLV 306 Solvay", Current Opinion in Investigational Drugs, 2003, vol. 4, No. 3, pp. 329-332.

Graul, "Annual Update 2003: Cardiovascular Drugs", Drugs of the Future, Barcelona, ES, 2003, vol. 28, No. 6, pp. 565-585.

Stella, "Prodrugs as therapeutics", Expert Opinion, Ther. Patents, 2004, vol. 14, No. 3, pp. 277-280.

Ettmayer et al., "Lessons learned from marketed and investigational prodrugs", Journal of Medicinal Chemistry, 2004, vol. 47, No. 10, pp. 2393-2404.

Sum et al., "Prodrugs of CL316243: A Selective $\beta_3$-Adrenergic Receptor Agonist for Treating Obesity and Diabetes", Bioorganic & Medicinal Chemistry Letters, 1999, vol. 9, pp. 1921-1926.

Yoshimura et al. "Preparation of 1 Acyloxyethyl Esters of 7-[2-(2-Aminothiazol-4-yl)Acetamido]-3-[[[1-(2-Dimethylaminoethyl)-1$H$-Tetrazol-5-YL]Thio]-Methyl]Ceph-3-EM-4- Carboxylic Acid (CEFOTIAM) and their Oral Absorption in Mice", The Journal of Antibiotics, 1986, vol. 39, No. 9, pp. 1329-1342.

Kubo et al. "Nonpeptide angiotensin II Receptor Antagonists. Synthesis and Biological Activity of Potential Prodrugs of Benzimidazole-7-carboxylic Acids[1]" J. Med. Chem., 1993, vol. 36, No, 16, pp. 2343-2349.

European Search Report dated Mar. 1, 2006 (nine (9) pages).

\* cited by examiner

PHARMACEUTICAL COMPOSITIONS COMPRISING NEP-INHIBITORS, INHIBITORS OF THE ENDOGENOUS ENDOTHELIN PRODUCING SYSTEM AND HMG COA REDUCTASE INHIBITORS

CROSS REFERENCE TO RELATED APPLICATIONS

The present application claims priority to U.S. Provisional Application Ser. No. 60/635,963, filed Dec. 15, 2004, the disclosure of which is herein incorporated by reference in its entirety.

FIELD OF THE INVENTION

The present invention relates to a novel combination therapy for cardiovascular diseases or conditions by a synergistic combination of at least one inhibitor of neutral endopeptidase (=NEP), at least one inhibitor of the endogenous endothelin producing system and at least one HMG CoA reductase inhibitor. Thus, the invention also relates to novel pharmaceutical compositions comprising NEP inhibitors, inhibitors of the endogenous endothelin producing system and HMG CoA reductase inhibitors and the use of said pharmaceutical composition in the prophylaxis or treatment of cardiovascular and/or metabolic disorders or diseases in mammals (including humans).

BACKGROUND OF THE INVENTION

From document EP 0 254 032 A2 it is known that NEP inhibitors can lower blood pressure under conditions where angiotensin converting enzyme (=ACE) inhibitors as a monotherapy are relatively ineffective. Further, this document discloses that NEP inhibitors may be combined with other drugs used in the treatment of hypertension, e.g. ACE inhibitors, to enhance the effects of those drugs. Consequently, pharmaceutical compositions comprising both a NEP inhibitor and an ACE inhibitor are described.

Although the beneficial role of NEP inhibiting compounds in the treatment or prevention of cardiovascular diseases, in particular essential hypertension, pulmonary hypertension and/or congestive heart failure, is widely acknowledged today, their profile of action as a monotherapy is still suffering from certain inherent deficiencies.

In congestive heart failure, as a result of the decreased cardiac output and the increase in peripheral resistance, backpressure phenomena of the blood occur in the pulmonary circulation and the heart itself. As a result, an increased wall tension of the heart muscle occurs in the area of the auricles and chambers. In such a situation, the heart functions as an endocrine organ and secretes, inter alia, the atrial natriuretic peptide (=ANP) into the bloodstream. Due to its marked vasodilatory and natriuretic/diuretic activity, ANP brings about both a reduction in the peripheral resistance and a decrease in the circulating blood volume. The consequence is a marked pre- and afterload decrease. This constitutes an endogenous cardioprotective mechanism. This positive endogenous mechanism is limited in that ANP has only a very short half-life in the plasma. The reason for this is that the hormone is very rapidly broken down by NEP. Therefore, pharmacological NEP inhibition rises ANP levels and thus promotes this cardioprotective mechanism.

In congestive heart failure, due to a disease-related reduced output of the heart, a reflex increase in peripheral vascular resistance occurs. As a result, the heart muscle must begin to pump against an increased afterload. In a vicious cycle, this results in increased strain on the heart and worsens the situation further. The increase in the peripheral resistance is mediated, inter alia, by the vasoactive peptide endothelin. Endothelin (=ET) is the strongest presently known endogenous vasoconstrictory substance and is formed from the precursor big endothelin (=bigET) with participation of the endothelin converting enzyme (=ECE). NEP is involved not only in the breakdown of ANP but also in the breakdown of ET.

For these reasons, a combination of compounds having NEP-inhibiting activity with compounds capable of inhibiting the endogenous endothelin producing system or compounds with dual inhibiting activities on NEP and the endogenous endothelin producing system would seem to provide added value in the therapy of cardiovascular diseases like essential hypertension, pulmonary hypertension and/or congestive heart failure. As a result of inhibition of the endogenous endothelin producing system, formation of endothelin would be prevented and thus an increase in peripheral resistance would be counteracted, to result in a relief of the strain on the heart muscle. Inhibition of the ANP degrading enzyme NEP can thus lead to higher ANP levels and an increased duration of action of ANP. This will lead to a reinforcement of the ANP-mediated endogenous cardioprotective mechanism of action. However, because NEP may also be involved in ET degradation, a pure NEP inhibition would, in addition to the desired increase in the ANP levels, also lead to an unfavorable increase in the ET levels. For this reason, a mixed profile with dually acting inhibition of NEP and of the endogenous endothelin producing system is to be regarded as particularly favorable, since it prevents both the breakdown of the natriuretically/diuretically acting ANP (by NEP-blockade), and simultaneously inhibits the formation of ET. As a result, the adverse attendant effect of pure NEP-inhibitors (increase in the endothelin levels) no longer comes to bear.

HMG CoA reductase inhibitors are pharmacologically active drug compounds which are capable of selectively inhibiting the enzyme 3-hydroxy-3-methylglutaryl-coenzyme A (=HMG-COA) reductase, the enzyme responsible for catalyzing the conversion of HMG CoA to mevalonate, which is an early and rate-limiting step in the cholesterol biosynthetic pathway. HMG CoA reductase inhibitors are therefore known to possess cholesterol lowering properties which make them valuable therapeutic agents in the treatment of vascular diseases or conditions. Several clinical studies have established that lowering certain forms of cholesterol in a mammal is an effective way to treat and prevent heart attacks, sudden death and angina pectoris, both in subjects having higher than normal levels of circulating cholesterol, as well as those having normal levels of cholesterol. Therefore lowering low-density lipoprotein (=LDL) cholesterol by administration of HMG CoA reductase inhibitors is today one of the primary objectives in the treatment of patients who have, or who are at risk of developing, cardiovascular diseases, such as atherosclerosis; cerebral infarction; coronary heart disease; myocardial infarction; restenosis, like restenosis following balloon angioplasty; and/or stroke.

However, the nature of cardiovascular, in particular hypertensive vascular, diseases is multifactorial. For example, hypertension frequently coexists with hyperlipidemia and both are considered to be major risk factors for developing cardiac disease ultimately resulting in adverse cardiac events. This clustering of risk factors is potentially due to a common mechanism. Coronary heart disease is known to be a multifactorial disease in which the incidence and severity are affected by the lipid profile, the presence of diabetes and the sex of the subject. Incidence is also affected by smoking and left ventricular hypertrophy which is secondary to hypertension. To meaningfully reduce the risk of coronary heart disease, it is therefore important to manage the entire risk spectrum. For example, hypertension intervention trials have failed to demonstrate full normalization in cardiovascular mortality due to coronary heart disease. Treatment with cholesterol synthesis inhibitors in patients with and without coronary artery disease reduces the risk of cardiovascular morbidity and mortality. Further, the use of a fixed, preferably low-dose combination agent potentially also offers lower doses of each component than those that may be necessary with monotherapy, thus reducing the risks of dose-dependent adverse events and associated compliance problems. Further, patient compliance with the management of hypertension is generally better than patient compliance with hyperlipidemia. It would therefore be advantageous for patients to have a combinatorial, preferably a single, therapy which treats both of these conditions.

Compounds with a dually acting combined inhibitory effect on NEP and the endogenous endothelin producing system, i.e. benzazepine-, benzoxazepine- and benzothiazepine-N-acetic acid derivatives, are known from document EP 0 733 642 A1 (=U.S. Pat. No. 5,677,297). Further favorable pharmacological properties of compounds falling within the structural scope of EP 0 733 642 A1 are known from documents EP 0 830 863 A1 (=U.S. Pat. No. 5,783,573), WO 00/48601 A1 (=U.S. Pat. No. 6,482,820) and WO 01/03699 A1 (=U.S. 2003-0040512-A1).

Phosphonic acid substituted benzazepinone-N-acidic acid derivatives with a combined inhibitory effect on NEP and the endogenous endothelin producing system are disclosed in document EP 0 916 679 A1 (=U.S. Pat. No. 5,952,327).

Amidomethyl-substituted 1-(carboxyalkyl)-cyclopentylcarbonylamino-benzazepine-N-acetic acid derivatives which are useful e.g. for the prophylaxis and/or treatment of cardiovascular conditions or diseases, are disclosed in document WO 2005/030795 A1.

From document WO 02/094176 A2 it is known that certain compounds, including those disclosed in document EP 0 733 642 A1 and in document EP 0 916 679 A1, may inhibit the endogenous endothelin producing system via an inhibition of metalloprotease IGS5. The metalloprotease IGS5 is also known as human soluble endopeptidase (=hSEP) and is described e.g. in document WO 02/094176 A2. Further, WO 02/094176 A2 discloses the use of compounds with combined NEP/hSEP inhibitory activity for the prophylaxis or treatment of inter alia cardiovascular diseases.

Document WO 99/47138 A1 provides pharmaceutical compositions comprising a matrix metalloprotease inhibitor and a statin for the treatment of vascular diseases.

International patent application WO 2004/082636 teaches a combination of an aldosterone receptor antagonist and a neutral endopeptidase inhibitor for i.a. treatment of cardiovascular diseases.

U.S. patent application No. 2004/0092573 discloses certain HMG CoA reductase inhibitors and their combinations with further active agents.

International patent application WO 02/092622 discloses certain dipeptide derivatives which can act as dual inhibitors of ACE and NEP as well as inhibitors of the endothelin converting enzyme (=ECE). A combination of said dipeptide derivatives with i.a. HMG CoA reductase inhibitors is likewise disclosed.

SUMMARY OF THE INVENTION

It is one object of the present invention to provide a novel combination therapy for treating or ameliorating cardiovascular disorders or diseases, especially angina pectoris; angina abdominalis; arrhythmias; atherosclerosis; cardiac hypertrophy; cerebral infarction; cerebral ischemias; congestive heart failure; coronary heart disease; hypertension, in particular essential hypertension, pulmonary hypertension, renal hypertension and/or hypertension associated with obesity; myocardial infarction; restenosis and/or stroke, with enhanced efficacy and a favorable safety profile. A further object of the present invention is to provide a novel combination therapy for treating or ameliorating metabolic disorders or diseases like the metabolic syndrome or syndrome X, in particular but not limited to metabolic disorders or diseases associated with obesity.

It has now surprisingly been found that a combination of at least one NEP-inhibitor, at least one inhibitor of the endogenous endothelin producing system and additionally at least one HMG CoA reductase inhibitor, provides still further enhanced efficacy in treating or ameliorating cardiovascular disorders or diseases like angina pectoris; angina abdominalis; arrhythmias; atherosclerosis; cardiac hypertrophy; cerebral infarction; cerebral ischemias; congestive heart failure; coronary heart disease; hypertension, in particular essential hypertension, pulmonary hypertension, renal hypertension and/or hypertension associated with obesity; myocardial infarction; restenosis and/or stroke, and a favorable safety profile. Furthermore, said combination of at least one NEP-inhibitor, at least one inhibitor of the endogenous endothelin producing system and additionally at least one HMG CoA reductase inhibitor provides further enhanced efficacy in treating or ameliorating metabolic disorders or diseases like the metabolic syndrome or syndrome X, in particular but not limited to metabolic disorders or diseases associated with obesity.

The invention therefore relates in a first aspect to pharmaceutical compositions comprising pharmacologically effective quantities of each of a) at least one NEP-inhibitor as a first active agent,
b) at least one inhibitor of the endogenous endothelin producing system as a second active agent and
c) at least one HMG CoA reductase inhibitor as a third active agent.

The pharmaceutical compositions according to the invention may further and preferably comprise conventional pharmaceutically acceptable auxiliaries and/or carriers.

In the pharmaceutical compositions according to the invention, the subcombination of at least one NEP-inhibitor (a) and at least one inhibitor of the endogenous endothelin producing system (b) can preferably be realized by a dually acting compound of general Formula I,

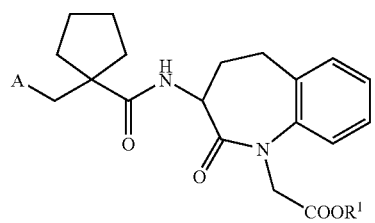

I wherein
$R^1$ is hydrogen or a group forming a biolabile carboxylic acid ester
A represents a group selected from the subgroups (a),

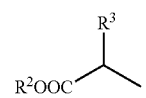

(a)

wherein
$R^2$ is hydrogen or a a group forming a biolabile carboxylic acid ester and $R^3$ is a phenyl-$C_{1-4}$-alkyl group which can optionally be substituted in the phenyl ring by $C_{1-4}$-alkyl, $C_{1-4}$-alkoxy or halogen; or a naphthyl-$C_{1-4}$-alkyl group; or (b),

 (b)

wherein $R^4$ is hydrogen or a group forming a biolabile phosphonic acid ester and $R^5$ is hydrogen or a group forming a biolabile phosphonic acid ester; or (c),

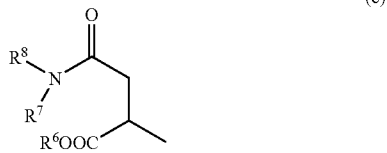 (c)

wherein $R^6$ is is hydrogen or a group forming a biolabile carboxylic acid ester, $R^7$ is hydrogen, $C_{1-4}$-alkyl or $C_{1-4}$-hydroxyalkyl, the hydroxyl group of which is optionally esterified with $C_{2-4}$-alkanoyl or an amino acid residue, and $R^8$ is $C_{1-4}$-alkyl; $C_{1-4}$-alkoxy-$C_{1-4}$-alkyl; $C_{1-4}$-hydroxyalkyl, which is optionally substituted by a second hydroxyl group and the hydroxyl groups of which are each optionally esterified with $C_{2-4}$-alkanoyl or an amino acid residue; $(C_{0-4}$-alkyl$)_2$amino-$C_{1-6}$-alkyl; $C_{3-7}$-cycloalkyl; $C_{3-7}$-cycloalkyl-$C_{1-4}$-alkyl; phenyl-$C_{1-4}$-alkyl, the phenyl group of which is optionally substituted 1-2 times by $C_{1-4}$-alkyl, $C_{1-4}$-alkoxy and/or halogen; naphthyl-$C_{1-4}$-alkyl; $C_{3-6}$-oxoalkyl; phenylcarbonylmethyl, the phenyl group of which is optionally substituted 1-2 times by $C_{1-4}$-alkyl, $C_{1-4}$-alkoxy and/or halogen, or 2-oxoazepanyl, or $R^7$ and $R^8$ together are $C_{4-7}$-alkylene, the methylene groups of which are optionally replaced 1-2 times by carbonyl, nitrogen, oxygen and/or sulphur and which are optionally substituted once by hydroxy, which is optionally esterified with $C_{2-4}$-alkanoyl or an amino acid residue; $C_{1-4}$-alkyl; $C_{1-4}$-hydroxyalkyl, the hydroxyl group of which is optionally esterified with $C_{2-4}$-alkanoyl or an amino acid residue; phenyl or benzyl, and/or physiologically compatible salts of acids of Formula I and/or physiologically compatible acid addition salts of compounds of Formula Ic.

Where the substituents in the compounds of Formula I are or contain $C_{1-4}$-alkyl groups, these may be straight-chain or branched. Where biolabile ester forming groups in the compounds of Formula I are or contain lower alkyl groups, these may be straight-chain or branched and contain usually 1 to 4 carbon atoms. Where the substituents contain halogen, fluorine, chlorine or bromine, preferably fluorine or chlorine are particularly suitable. Where substituents contain $C_{2-4}$-alkanoyl, this may be straight-chain or branched. Acetyl is preferred as $C_{2-4}$-alkanoyl.

Where substituents are biolabile ester forming groups, these as a rule represent prodrugs of the active drug prinicple. Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (see e.g. Medicinal Chemistry: Principles and Practice, 1994, ISBN 0-85186-494-5, Ed.: F. D. King, p. 215; J. Stella, "*Prodrugs as therapeutics*", Expert Opin. Ther. Patents, 14(3), 277-280, 2004; P. Ett-mayer et al., "*Lessons learned from marketed and investigational prodrugs*", J. Med. Chem., 47, 2393-2404, 2004).

Suitable physiologically compatible salts of free acids or partial esters of Formula I include their alkali metal, alkaline earth metal or ammonium salts, for example sodium or calcium salts or salts with physiologically compatible, pharmacologically neutral organic amines such as, for example, diethylamine or tert.-butylamine.

Preferred are the compounds of general Formula Ia,

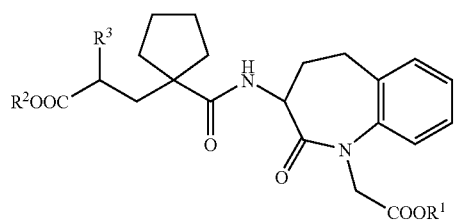 Ia wherein $R^1$, $R^2$ and $R^3$ have the above meanings, and physiologically compatible salts of acids of Formula Ia. Preferred salts of compounds of Formula Ia are e.g. disclosed in document WO 03/059939 A1 which is incorporated herein by reference in its entirety. The compounds of Formula Ia contain two chiral carbon atoms, namely the carbon atom which is in the 3 position of the ring framework (=3-position) and bears the amide side-chain, and the carbon atom of the amide side-chain which bears the radical $R^3$(=2'-position). The compounds can therefore exist in several optically active stereoisomeric forms or as a racemate. According to the present invention both the racemic mixtures and the isomerically pure compounds of Formula Ia may be used.

The compounds of Formula Ia are optionally esterified dicarboxylic acid derivatives. Depending on the form of administration, biolabile monoesters, particularly compounds in which $R^2$ is a group forming a biolabile ester and $R^1$ is hydrogen, or dicarboxylic acids are preferred, the latter being particularly suitable for i.v. administration. Groups which can be cleaved under physiological conditions in vivo, releasing bioavailable derivatives of the compounds of Formula Ia, are suitable as groups forming biolabile carboxylic acid esters $R^1$ and $R^2$. Suitable examples of this are $C_{1-4}$-alkyl groups, in particular methyl, ethyl, n-propyl and isopropyl; $C_{1-4}$-alkyloxy-$C_{1-4}$-alkyloxy-$C_{1-4}$-alkyl groups, in particular methoxyethoxymethyl; $C_{3-7}$-cycloalkyl groups, in particular cyclohexyl; $C_{3-7}$Cycloalkyl-$C_{1-4}$-alkyl groups, in particular cyclopropylmethyl; N,N-di-($C_{0-4}$-alkyl)amino-$C_{1-6}$-alkyl groups; phenyl or phenyl-$C_{1-4}$-alkyl groups optionally substituted in the phenyl ring once or twice by halogen, $C_{1-4}$-alkyl or $C_{1-4}$-alkoxy or by a $C_{1-4}$-alkylene chain bonded to two adjacent carbon atoms; dioxolanylmethyl groups optionally substituted in the dioxolane ring by $C_{1-4}$-alkyl; $C_{2-6}$- alkanoyloxy-$C_{1-4}$-alkyl groups optionally substituted at the oxy-$C_{1-4}$-alkyl group by $C_{1-4}$-alkyl; double esters like 1-[[($C_{1-4}$-alkyl)carbonyl]oxy]$C_{1-4}$-alkyl esters, e.g. (RS)-1-[[(isopropyl)carbonyl]oxy]ethyl or (RS)-1-[[(ethyl)carbonyl]oxy]-2-methylpropyl (for preparation see e.g. F. W. Sum et al., Bioorg. Med. Chem. Lett. 9 (1999) 1921-1926 or Y. Yoshimura et al., The Journal of Antibiotics 39/9 (1986) 1329-1342 ); carbonate esters like 1-[[($C_{4-7}$-cycloalkyloxy) carbonyl]oxy] $C_{1-4}$-alkyl esters, preferably (RS)-1-[[(cyclohexyloxy)carbonyl]oxy]ethyl (=cilexetil; for preparation see e.g. K. Kubo et al., J. Med. Chem. 36 (1993) 2343-2349, cited as "Kubo et al." hereinafter)) or 2-oxo-1,3-dioxolan-4-yl-$C_{1-4}$-alkyl esters which optionally contain a double bond in the dioxolan ring, preferably 5-methyl-2-oxo-1,3-dioxolen-4-yl-methyl (=medoxomil, for preparation see e.g. Kubo et al.) or 2-oxo-1,3-dioxolan-4-yl-methyl (=(methyl)ethylenecarbonate). Where the group forming a biolabile ester represents an optionally substituted phenyl-$C_{1-4}$-alkyl group, this may contain an alkylene chain with 1 to 3, preferably 1, carbon atoms and preferably stands for optionally substituted benzyl, in particular for 2-chlorobenzyl or 4-chlorobenzyl. Where the group forming a biolabile ester represents an optionally substituted phenyl group, the phenyl ring of which is substituted by a lower alkylene chain, this may contain 3 to 4, preferably 3, carbon atoms and in particular be indanyl. Where the group forming a biolabile ester represents an optionally substituted $C_{2-6}$-alkanoyloxy-$C_{1-4}$-alkyl group, the $C_{2-6}$-alkanoyl group may be straight-chain or branched.

$R^1$ preferably has the meanings hydrogen, $C_{1-4}$-alkyl, p-methoxybenzyl, N,N-di-($C_{0-4}$-alkyl)amino-$C_{1-6}$-alkyl, (RS)-1-[[(isopropyl)carbonyl]oxy]ethyl, (RS)-1-[[(ethyl)carbonyl]oxy]-2-methylpropyl, (RS)-1-[[(cyclohexyloxy) carbonyl]oxy]ethyl, 5-methyl-2-oxo-1,3-dioxolen-4-yl-methyl, 2-oxo-1,3-dioxolan-4-yl-methyl or (RS)-1-[[(ethoxy) carbonyl]oxy]ethyl.

$R^2$ preferably has the meanings hydrogen, ethyl, methoxyethoxymethyl, (RS)-1-[[(isopropyl)carbonyl]oxy]ethyl, (RS)-1-[[(ethyl)carbonyl]oxy]-2-methylpropyl, (RS)-1-[[(cyclohexyloxy)carbonyl]oxy]ethyl, 5-methyl-2-oxo-1,3-dioxolen-4-yl-methyl, 2-oxo-1,3-dioxolan-4-yl-methyl or (RS)-1-[[(ethoxy)carbonyl]oxy]ethyl.

More preferred are the compounds which are selected from the group consisting of 2-[1-(1-carboxymethyl-2-oxo-2,3,4,5-tetrahydro-1H-benzo[b]azepin-3-ylcarbamoyl)-cyclopentylmethyl]-4-phenyl-butyric acid ethyl ester [alternative name: 3-[1-{2'-(ethoxycarbonyl)}-4'-phenylbutyl]-cyclopentan-1-carbonylamino]-2,3,4,5-tetrahydro-2-oxo-1H-1-benzazepin-1-acetic acid] of Formula II,

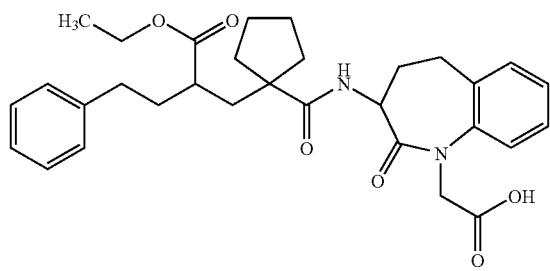

II

2-[1-(1-carboxymethyl-2-oxo-2,3,4,5-tetrahydro-1H-benzo[b]azepin-3-ylcarbamoyl)-cyclopentylmethyl]-4-naphthalen-1-yl-butyric acid ethyl ester [alternative name: 3-[1-{2-(ethoxycarbonyl)-4-(1-naphthyl)butyl]cyclopentyl}carbonyl)amino]-2-oxo-2,3,4,5-tetrahydro-1H-1-benzazepin-1-yl}acetic acid] of Formula III,

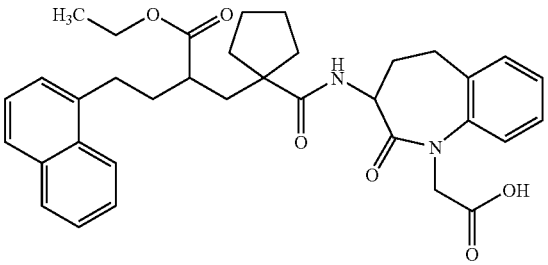

III

2-[1-(1-carboxymethyl-2-oxo-2,3,4,5-tetrahydro-1H-benzo[b]azepin-3-ylcarbamoyl)-cyclopentylmethyl]-4-phenyl-butyric acid of Formula IV,

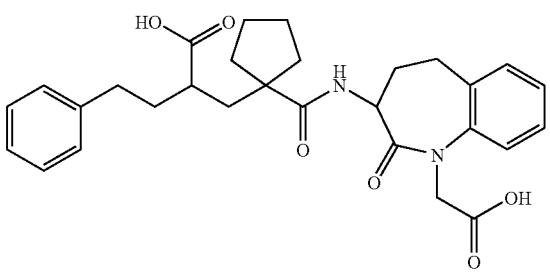

IV

2-[1-(1-carboxymethyl-2-oxo-2,3,4,5-tetrahydro-1H-benzo[b]azepin-3-ylcarbamoyl)-cyclopentylmethyl]-4-naphthalen-1-yl-butyric acid of Formula V,

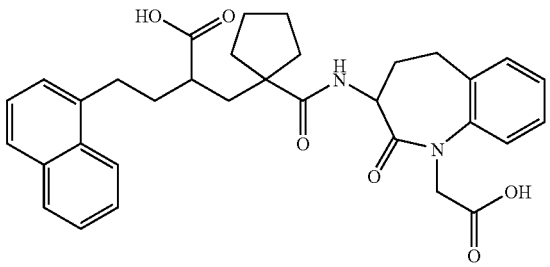

V and physiologically compatible salts of the acids of Formulas II, III, IV and/or V. The compounds of Formulas II, III, IV and V are especially suited in their 3S,2'R forms. Most preferred is the compound of Formula II in its 3S,2'R form, also known as "daglutril" or "SLV306". The compounds of Formula Ia are known, for example, from document EP 0 733 642 A1 which is incorporated herein by reference in its entirety, and can be produced according to the production processes disclosed or referenced in this document or analogously to said production processes.

Further, compounds of general Formula Ib,

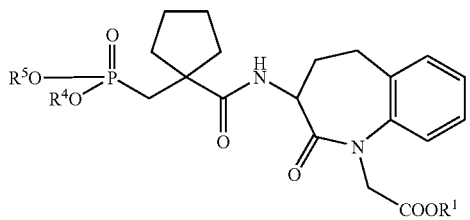

wherein $R^1$, $R^4$ and $R^5$ have the meanings given above, or physiologically compatible salts of acids of Formula Ib can be used as dually acting compounds capable of inhibiting NEP and the endogenous endothelin producing system. The compounds of Formula Ib are known, for example, from document EP 0 916 679 A1 which is incorporated herein by reference in its entirety, and can be produced according to the production processes disclosed or referenced in this document or analogously to said production processes.

Suitable groups $R^1$ forming biolabile carboxylic acid esters in compounds of Formula Ib are those as specified for compounds of Formula Ia above.

Groups $R^4$ and $R^5$ suitable as groups forming biolabile phosphonic acid esters are those which can be removed under physiological conditions in vivo with release of the respective phosphonic acid function. For example, groups which are suitable for this purpose are lower alkyl groups, $C_2$-$C_6$-alkanoyloxymethyl groups optionally substituted on the oxymethyl group by lower alkyl, or phenyl or phenyl-lower alkyl groups whose phenyl ring is optionally mono- or polysubstituted by lower alkyl, lower alkoxy or by a lower alkylene chain bonded to two adjacent carbon atoms. If the group $R^4$ and/or $R^5$ forming a biolabile ester is or contains lower alkyl, this can be branched or unbranched and can contain 1 to 4 carbon atoms. If $R^4$ and/or $R^5$ are an optionally substituted alkanoyloxymethyl group, it can contain a preferably branched alkanoyloxy group having 2 to 6, preferably 3 to 5, carbon atoms and can, for example, be a pivaloyloxymethyl radical (=tert-butylcarbonyloxymethyl radical). If $R^4$ and/or $R^5$ are an optionally substituted phenyl-lower alkyl group, this can contain an alkylene chain having 1 to 3, preferably 1, carbon atoms. If the phenyl ring is substituted by a lower alkylene chain, this can contain 3 to 4, in particular 3, carbon atoms and the substituted phenyl ring is in particular indanyl.

The compounds of the formula Ib contain a chiral carbon atom, namely the carbon atom carrying the amide side chain in the 3-position of the benzazepine structure. The compounds can thus be present in two optically active stereoisomeric forms or as a racemate. The present invention includes both the racemic mixtures and the isomerically pure compounds of the formula I. If $R^4$ and $R^5$ in compounds of the formula Ib are not hydrogen and in each case have different meanings, the phosphorus atom of the phosphonic acid group can also be chiral. The invention also relates to the isomer mixtures and isomerically pure compounds of the formula Ib formed as a result of chiral phosphorus atoms.

When compounds of Formula Ib are used according to the invention, (3-{[1-(benzyloxy-ethoxy-phosphorylmethyl)-cyclopentanecarbonyl]-amino}-2-oxo-2,3,4,5-tetra-hydro-benzo[b]azepin-1-yl)-acetic acid tert-butyl ester and isobutyric acid 1-[[1-(-1-carboxymethyl-2-oxo-2,3,4,5-tetrahydro-1H-benzo[b]azepin-3-ylcarbamoyl)-cyclopentylmethyl]-(1-isobutyryloxy-ethoxy)-phosphinoyloxy]-ethyl ester are preferred. Both of said compounds are particularly preferred when the stereochemistry at the chiral carbon atom (see above) is "S", namely in their "(3S)" configuration. The compounds of Formula Ib are known, for example, from document EP 0 916 679 A1, and can be produced according to the production processes disclosed or referenced in this document or analogously to said production processes.

Also preferred are the compounds of general Formula Ic,

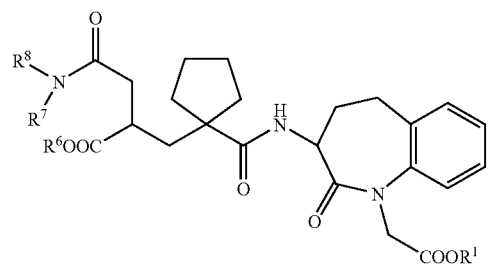

wherein $R^1$, $R^6$, $R^7$ and $R^8$ have the above meanings, and physiologically compatible salts of acids of Formula Ic and/or physiologically compatible acid addition salts of compounds of Formula Ic, for the use as dually acting compounds capable of inhibiting NEP and the endogenous endothelin producing system in pharmacological compositions according to the invention. The compounds of Formula Ic are known, for example, from document WO 2005/030795 A1 which is incorporated herein by reference in its entirety, and can be produced according to the production processes disclosed or referenced in this document or analogously to said production processes.

Where in compounds of Formula Ic the substituents $R^7$ and/or $R^8$ contain basic groups, in particular nitrogen, the compounds of Formula Ic may also occur in the form of acid addition salts. Physiologically compatible acid addition salts of compounds of Formula Ic are their conventional salts with inorganic acids, for example sulphuric acid, phosphoric acid or hydrohalic acids, preferably hydrochloric acid, or with organic acids, for example lower aliphatic monocarboxylic, dicarboxylic or tricarboxylic acids such as maleic acid, fumaric acid, tartaric acid, citric acid, or with sulphonic acids, for example lower alkanesulphonic acids such as methanesulphonic acid.

Suitable groups $R^1$ forming biolabile carboxylic acid esters in compounds of Formula Ic are those as specified for compounds of Formula Ia above. Suitable groups $R^6$ forming biolabile carboxylic acid esters in compounds of Formula Ic are the same as specified for groups $R^2$ in compounds of Formula Ia above.

$R^7$ preferably has the meanings hydrogen, methyl, ethyl, 2-hydroxyethyl or 3-hydroxypropyl, each hydroxyl group optionally being esterified with $C_{2-4}$-alkanoyl or an amino acid residue.

Where $R^8$ has the meaning $(C_{0-4}$-alkyl$)_2$amino-$C_{1-6}$-alkyl, one or two $C_{0-4}$-alkyl groups can independently of each other be present. More specifically, "$(C_{0-4}$-alkyl$)_2$amino-$C_{1-6}$-alkyl" expressly comprises the meanings "$(C_0)_2$-alkylamino-$C_{1-6}$-alkyl", "$(C_0)(C_{1-4})$-alkyl-amino-$C_{1-6}$-alkyl" and "$(C_{1-4})_2$-alkylamino-$C_{1-6}$-alkyl". "$(C_0)_2$-alkylamino-$C_{1-6}$-alkyl" is meant to denominate an unsubstituted primary (=—$NH_2$) amino group bonded to $C_{1-6}$-alkyl(en); "$(C_0)$ (C$_{1-4}$)-alkylamino-C$_{1-6}$-alkyl" is meant to denominate a secondary amino group mono-substituted by (C$_{1-4}$)-alkyl and bonded to C$_{1-6}$-alkyl(en); "(C$_{1-4}$)$_2$-alkylamino-C$_{1-6}$-alkyl" is meant to denominate a tertiary amino group disubstituted by (C$_{1-4}$)-alkyl and bonded to C$_{1-6}$-alkyl(en). R$^8$ preferably has the meanings isopropyl; methoxyethyl; 2-hydroxyethyl or 3-hydroxypropyl, each hydroxyl group optionally being esterified with C$_{2-4}$-alkanoyl or an amino acid residue; 3-acetyloxy-n-propyl; cyclopropylmethyl; 2-methoxybenzyl; 4-methoxybenzyl; 4-methoxyphenylethyl; 2,4-dimethoxybenzyl; 1-naphthylmethyl; 3-oxo-1,1-dimethylbutyl; phenyl-2-oxoethyl; 2-(4-methoxyphenyl)-2-oxoethyl; 3-(2-oxoazepanyl); (C$_{0-4}$-alkyl)$_2$amino-C$_{1-6}$-alkyl, in particular dimethylamino-n-propyl, (methyl)aminoethyl, amino-n-propyl, amino-n-butyl or amino-n-pentyl.

Where R$^7$ and R$^8$ together are C$_{4-7}$-alkylene, the methylene groups of which are optionally replaced or optionally substituted, in each case morpholine; piperidine; 4-ketopiperidine; 4-hydroxypiperidine, optionally being esterified with C$_{2-4}$-alkanoyl or an amino acid residue at the hydroxyl group; piperazine or pyrrolidine is preferred.

Where in the compounds of Formula Ic hydroxyl groups are esterified with amino acid residues, these amino acid residues may be derived from natural or non-natural, α- or β-amino acids. Suitable amino acids which can be used are for example selected from the group cosisting of alanine, 2-aminohexanoic acid (=norleucine), 2-aminopentanoic acid (=norvaline), arginine, asparagine, aspartic acid, cysteine, 3,4-dihydroxyphenylalanine (=dopa), glutamine, glutamic acid, glycine, histidine, isoleucine, leucine, lysine, methionine, ornithine (=2,5-diaminovaleric acid), 5-oxo-2-pyrrolidinecarbonic acid (=pyroglutamic acid), phenylalanine, proline, serine, threonine, thyronine, tryptophan, tyrosine and valine. Preferred are amino acid residues which are derived from alanine, asparagine, glutamine, glycine, isoleucine, leucine, lysine, ornithine, phenylalanine, proline and valine.

The compounds of Formula Ic contain two chiral carbon atoms, namely the carbon atom bearing the amide side chain in position 3 of the benzazepine skeleton (=C$_b$*) and the carbon atom bearing the radical "—COOR$^6$" (=C$_a$*). The compounds can thus be present in a total of four stereoisomeric forms. The present invention comprises both the mixtures of stereoisomers and enantiomers, and also the isomerically pure compounds of Formula Ic. Isomerically pure compounds of Formula Ic are preferred. Particularly preferred are compounds of Formula Ic wherein the carbon atom bearing the amide side chain in position 3 of the benzazepine skeleton is in the "S" configuration. With respect to the chiral carbon atom "*C$_a$" bearing the radical "—COOR$^6$", the configuration of the compounds of Formula I which is preferred according to the invention in the context of this invention is provisionally assigned the configuration designation "rel1". It can be derived by analogous observations of suitable compounds of known configuration that the preferred configuration "rel1" at the chiral centre "*C$_a$" is probably likewise the "S" configuration.

Particularly preferred compounds of Formula Ic are selected from the group consisting of 2-{[1-({[1-(carboxymethyl)-2-oxo-2,3,4,5-tetrahydro-1H-1-benzazepin-3-yl]amino}-carbonyl)cyclopentyl]methyl}-4-[isopropyl(methyl)amino]-4-oxobutanoic acid;

2-{[1-({[1-(carboxymethyl)-2-oxo-2,3,4,5-tetrahydro-1H-1-benzazepin-3-yl]amino}-carbonyl)cyclopentyl]methyl}-4-(dimethylamino)-4-oxobutanoic acid;

2-{[1-({[1-(carboxymethyl)-2-oxo-2,3,4,5-tetrahydro-1H-1-benzazepin-3-yl]amino}-carbonyl)cyclopentyl]methyl}-4-(diethylamino)-4-oxobutanoic acid;

2-{[1-({[1-(carboxymethyl)-2-oxo-2,3,4,5-tetrahydro-1H-1-benzazepin-3-yl]amino}carbonyl)cyclopentyl]methyl}-4-[(2-hydroxyethyl)(methyl)amino]-4-oxobutanoic acid;

2-{[1-({[1-(carboxymethyl)-2-oxo-2,3,4,5-tetrahydro-1H-1-benzazepin-3-yl]amino}carbonyl)cyclopentyl]methyl}-4-[(3-hydroxypropyl)(methyl)amino]-4-oxobutanoic acid;

2-{[1-({[1-(carboxymethyl)-2-oxo-2,3,4,5-tetrahydro-1H-1-benzazepin-3-yl]amino}-carbonyl)cyclopentyl]methyl}-4-(4-hydroxypiperidin-1-yl)-4-oxobutanoic acid;

2-{[1-({[1-(carboxymethyl)-2-oxo-2,3,4,5-tetrahydro-1H-1-benzazepin-3-yl]amino}-carbonyl)cyclopentyl]methyl}-4-oxo-4-[4-(L-valyloxy)piperidin-1-yl]butanoic acid;

2-{[1-({[1-(carboxymethyl)-2-oxo-2,3,4,5-tetrahydro-1H-1-benzazepin-3-yl]amino}-carbonyl)cyclopentyl]methyl}-4-morpholin-4-yl-4-oxobutanoic acid;

2-{[1-({[1-(carboxymethyl)-2-oxo-2,3,4,5-tetrahydro-1H-1-benzazepin-3-yl]amino}-carbonyl)cyclopentyl]methyl}-4-oxo-4-(4-oxopiperidin-1-yl)butanoic acid;

4-[bis(2-hydroxyethyl)amino]-2-{[1-({[1-(carboxymethyl)-2-oxo-2,3,4,5-tetrahydro-1H-1-benzazepin-3-yl]amino}carbonyl)cyclopentyl]methyl}-4-oxobutanoic acid;

2-{[1-({[1-(carboxymethyl)-2-oxo-2,3,4,5-tetrahydro-1H-1-benzazepin-3-yl]amino}carbonyl)cyclopentyl]methyl}-4-{ethyl[3-(ethylamino)propyl]amino}-4-oxobutanoic acid;

2-{[1-({[1-(carboxymethyl)-2-oxo-2,3,4,5-tetrahydro-1H-1-benzazepin-3-yl]amino}-carbonyl)cyclopentyl]methyl}-4-[[2-(dimethylamino)ethyl](methyl)amino]-4-oxobutanoic acid;

4-[(3-aminopropyl)(ethyl)amino]-2-{[1-({[1-(carboxymethyl)-2-oxo-2,3,4,5-tetrahydro-1H-1-benzazepin-3-yl]amino}carbonyl)cyclopentyl]methyl}-4-oxobutanoic acid, 2-{[1-({[1-(carboxymethyl)-2-oxo-2,3,4,5-tetrahydro-1H-1-benzazepin-3-yl]amino}-carbonyl)cyclopentyl]methyl}-4-{methyl[2-(methylamino)ethyl]amino}-4-oxobutanoic acid;

4-[(4-aminobutyl)(methyl)amino]-2-{[1-({[1-(carboxymethyl)-2-oxo-2,3,4,5-tetrahydro-1H-1-benzazepin-3-yl]amino}carbonyl)cyclopentyl]methyl}-4-oxobutanoic acid;

4-[(4-aminobutyl )(ethyl)amino]-2-{[1-({[1-(carboxymethyl)-2-oxo-2,3,4,5-tetrahydro-1H-1-benzazepin-3-yl]amino}carbonyl)cyclopentyl]methyl}-4-oxobutanoic acid;

2-{[1-({[1-(carboxymethyl)-2-oxo-2,3,4,5-tetrahydro-1H-1-benzazepin-3-yl]amino}-carbonyl)cyclopentyl]methyl}-4-{methyl[3-(methylamino)propyl]amino}-4-oxobutanoic acid and 4-[(5-aminopentyl)(methyl)amino]-2-{[1-({[1 -(carboxymethyl)-2-oxo-2,3,4,5-tetrahydro-1H-1-benzazepin-3-yl]amino}carbonyl)cyclopentyl]methyl}-4-oxobutanoic acid, together with their biolabile esters and physiologically compatible salts of acids of these compounds of Formula Ic and/or physiologically compatible acid addition salts of these compounds of Formula Ic.

Inhibitors of the endogenous endothelin producing system can be selected from the group consisting of inhibitors of ECE, inhibitors of hSEP and dually acting compounds capable of inhibiting ECE and hSEP.

HMG CoA reductase inhibitors which can be used according to the present invention are understood to comprise any physiologically compatible salt, solvate, prodrug or ester thereof and may be selected from the group consisting of atorvastatin, berivastatin, cerivastatin, crilvastatin, fluvastatin, glenvastatin, lovastatin, mevastatin, pitavastatin, pravastatin, rosuvastatin, simvastatin, tempostatin or any physiologically compatible salts, solvates, prodrugs or esters thereof. Atorvastatin, fluvastatin, lovastatin, pravastatin, and/or simvastatin are preferred HMG CoA reductase inhibitors. Most preferred are atorvastatin, pravastatin and/or simvastatin. HMG CoA reductase inhibitors are known per se, e.g. from documents U.S. Pat. Nos. 4,681,893; 5,082,859; 5,006,530; 5,134,157; 4,739,073; 4,925,852; 4,231,938; 4,049,495; 5,011,930; 4,346,227; 5,260,440; 4,444,784 and 6,028,075 the disclosures of all of said documents being incorporated herein by reference.

Further pharmaceutical .compositions which can be favorably used in the treatment and/or prophylaxis of cardiovascular conditions or diseases comprise pharmacologically effective quantities of each of a) at least one NEP-inhibitor as a first active agent,
b) at least one inhibitor of the endogenous endothelin producing system as a second active agent and
d) at least one calcium channel blocking agent as a third or further active agent.

The NEP-inhibitors and the inhibitors of the endogenous endothelin producing system or their combinations are the same as described hereabove. Suitable calcium channel blocking agents (=calcium antagonists) can be selected from the group consisting of amlodipine, felodipine, isradipine, nicardipine, nifedipine, nilvadipine, nimodipine, nisoldipine, nitrendipine; gallopamil, verapamil; diltiazem and fendiline; and any of their physiologically compatible salts. Preferably, the calcium channel blocking agents may be administered together with a drug selected from the group consisting of 2-[1-(1-carboxymethyl-2-oxo-2,3,4,5-tetrahydro-1H-benzo[b]azepin-3-ylcarbamoyl)-cyclopentylmethyl]-4-phenylbutyric acid ethyl ester; 2-[1-(1-carboxymethyl-2-oxo-2,3,4,5-tetrahydro-1H-benzo[b]-azepin-3-ylcarbamoyl)-cyclopentylmethyl]-4-naphthalen-1-yl-butyric acid ethyl ester; 2-[1-(1-carboxymethyl-2-oxo-2,3,4,5-tetrahydro-1H-benzo[b]azepin-3-ylcarbamoyl)-cyclopentylmethyl]-4-phenyl-butyric acid; 2-[1-(1-carboxymethyl-2-oxo-2,3,4,5-tetrahydro-1H-benzo[b]azepin-3-ylcarbamoyl)-cyclopentylmethyl]-4-naphthalen-1-yl-butyric acid; and their physiologically compatible salts. More preferred, the calcium channel blocking agents may be administered together with daglutril or its physiologically compatible salts.

The pharmaceutical compositions according to the present invention can further comprise or be administered in combination with one or more other cardiovascular active agents, in particular antihypertensives and/or diuretics. The pharmaceutical compositions according to the invention can be prepared in a manner known per se and thus can be obtained as formulations suitable for enteral, such as oral or rectal, or parenteral administration to mammals (including humans), comprising a therapeutical effective amount of the pharmacologically active agents, alone or in combination with one or more pharmaceutically acceptable auxiliaries and/or carriers, especially suitable for enteral or parenteral application. Pharmaceutical compositions for enteral or parenteral administration are, for example, in unit dosage forms, such as coated tablets, tablets, capsules or suppositories and also ampoules. These are prepared in a manner which is known per se, for example using conventional mixing, granulation, coating, solubulizing or lyophilizing processes. Typical oral formulations include coated tablets, tablets, capsules, syrups, elixirs and suspensions. Capsules may contain the active agents e.g. in form of powders, granules, pellets, beadlets or microtablets. For example, a pharmaceutical composition according to the invention may consist of from about 0.1% to 90%, preferably of from about 1% to about 80%, of the active agents, the rest being made up by pharmaceutically acceptable auxiliaries and/or carriers. Thus, pharmaceutical compositions for oral use can be obtained by combining the active compounds with solid excipients, if desired granulating a mixture which has been obtained, and, if required or necessary, processing the mixture or granulate into tablets or coated tablet cores after having added suitable auxiliary substances. Typical injectable formulations include solutions and suspensions.

In one embodiment of the pharmaceutical compositions according to the invention, the active agents (a), (b) and (c) can be obtained and administered together, e.g. in one combined unit dosage form like in one tablet or capsule, i.e. in a physical combination. In such a combined unit dosage form, the different active agents (a), (b) and (c) can be segregated from each other, e.g. by means of different layers in said tablet, e.g. by the use of inert intermediate layers known in the art; or by means of different compartments in said capsule. When a dually acting compound capable of inhibiting NEP and the endogenous endothelin producing system is used to embody the combination of active agents (a) and (b), the active agents [(a)+(b)] and (c) in the pharmaceutical composition can favorably be present in two separate dosage forms, e.g. as two different tablets or capsules, usually further comprising pharmaceutically acceptable auxiliaries and/or carriers, or in different compartments of one single capsule. Thus, in this embodiment at least the HMG CoA reductase inhibitor is present in a unit single dosage form physically segregated from the other active agent(s). The corresponding active agents or their pharmaceutically acceptable salts may also be used in form of their hydrates or include other solvents used for crystallization. A unit dosage form may be a fixed combination. A unit dosage form, in particular a fixed combination of the active agents (a), (b) and (c) is a preferred alternative of this embodiment.

In another embodiment the active agents (a), (b) and (c) can be obtained and administered in two or more separate unit dosage forms, e.g. in two or more tablets or capsules, the tablets or capsules being physically segregated from each other. The two or more separate unit dosage forms can be administered simultaneously or stepwise (separately), e.g. sequentially one after the other in either order. Thus, the active agents can be administered in either order at the same time or at different times spread over the day, the optimal dosage regimen usually being determined by prescription of a physician.

The typical pharmaceutically acceptable auxiliaries and/or carriers for use in the formulations described above are exemplified by: sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols; and hydrolyzed cereal solids, as well as other non-toxic compatible fillers, binders, disintegrants, agents, e.g.

talcum; buffers, preservatives, antioxidants, lubricants, flavoring and the like commonly used in pharmaceutical formulations.

In a specific embodiment of said first aspect, the invention also relates to a kit comprising in separate containers in a single package pharmaceutical dosage forms for use in combination, comprising, i1) in one separate container a pharmaceutical dosage form comprising at least one neutral endopeptidase inhibitor and in a second separate container a pharmaceutical dosage form comprising at least one inhibitor of the endogenous endothelin producing system, or i2) in one separate container a pharmaceutical dosage form comprising a dually acting compound capable of inhibiting neutral endopeptidase and the endogenous endothelin producing system, and ii) in another separate container a pharmaceutical dosage form comprising at least one HMG CoA reductase inhibitor.

The kit form is particularly advantageous but not limited to the case when the separate components must be administered in different dosage forms or are administered at different dosage intervals. The dosage forms may favorably be oral formulations like tablets or capsules. The separate containers may e.g. be blister packs—in particular where the oral formulations are tablets or coated tablets, boxes or other containers commonly used to package pharmaceutical dosage forms. Preferred are alternatives of the kit which comprise in one separate container a pharmaceutical dosage form comprising a dually acting compound capable of inhibiting neutral endopeptidase and the endogenous endothelin producing system, and in another separate container a pharmaceutical dosage form comprising at least one HMG CoA reductase inhibitor.

In a second aspect, the invention also relates to a use of at least one NEP-inhibitor in combination with at least one inhibitor of the endogenous endothelin producing system and at least one HMG CoA reductase inhibitor, for the preparation of a pharmaceutical composition or medicament for the prophylaxis or treatment of a cardiovascular disease, in particular angina pectoris; angina abdominalis; arrhythmias; atherosclerosis; cardiac hypertrophy; cerebral infarction; cerebral ischemias; congestive heart failure; coronary heart disease; hypertension, in particular essential hypertension, pulmonary hypertension, renal hypertension and/or hypertension associated with obesity; myocardial infarction; restenosis and/or stroke. In another embodiment of said second aspect, the present invention also relates to a use of at least one NEP-inhibitor in combination with at least one inhibitor of the endogenous endothelin producing system and at least one HMG CoA reductase inhibitor, for the preparation of a pharmaceutical composition or medicament for the prophylaxis or treatment of a metabolic disorder or disease like the metabolic syndrome or syndrome X, in particular but not limited to metabolic disorders or diseases associated with obesity.

The term "metabolic syndrome" as used in this application is meant to cover a complex of clinical pictures which—besides central obesity—mainly comprises hypertension, in particular arterial hypertension; insulin resistance, in particular diabetes mellitus type II; glucose intolerance; dyslipoproteinaemia, in particular as hypertriglyceridaemia, accompanied by dyslipoproteinaemia occurring with lowered HDL-cholesterol, and also hyperuricaemia, which can lead to gout.

In a third aspect, the invention relates to a method of treating or preventing a cardiovascular disease in mammals (including humans) comprising administering to a subject in need thereof an effective amount of a combination of at least one NEP-inhibitor, at least one inhibitor of the endogenous endothelin producing system and at least one HMG CoA reductase inhibitor. Subjects in need of such treatments are in particular those humans or mammals who are suffering from or being susceptible to a cardiovascular disease, in particular angina pectoris; angina abdominalis; arrhythmias; atherosclerosis; cardiac hypertrophy; cerebral infarction; cerebral ischemias; congestive heart failure; coronary heart disease; hypertension, in particular essential hypertension, pulmonary hypertension, renal hypertension and/or hypertension associated with obesity; myocardial infarction; restenosis and/or stroke.

In another embodiment of said third aspect, the present invention also relates to a method of treating or preventing metabolic disorders or diseases like the metabolic syndrome or syndrome X, in particular but not limited to metabolic disorders or diseases associated with obesity in mammals (including humans), comprising administering to a subject in need thereof an effective amount of a combination of at least one NEP-inhibitor, at least one inhibitor of the endogenous endothelin producing system and at least one HMG CoA reductase inhibitor. Subjects in need of such treatments are in particular those humans or mammals who are suffering from or being susceptible to insulin resistance, in particular diabetes mellitus type II; glucose intolerance; dyslipoproteinaemia, in particular as hypertriglyceridaemia, accompanied by dyslipoproteinaemia occurring with lowered HDL-cholesterol, and also hyperuricaemia.

In one specific embodiment of said third aspect, a fixed combination of a dually acting compound capable of inhibiting neutral endopeptidase and the endogenous endothelin producing system, and a HMG CoA reductase inhibitor can be used. Fixed combinations comprising daglutril and pravastatin, daglutril and simvastatin or daglutril and atorvastatin are preferred alternatives of this specific embodiment. More preferred alternatives of this embodiment are fixed combinations comprising daglutril and simvastatin or daglutril and atorvastatin.

For simplicity and illustrative purposes, the principles of the present invention are described by referring to various examples. One of ordinary skill in the art will readily recognize that the same principles are equally applicable to, and can be implemented in other forms, and that any such variation would be within those modifications that do not part from the true spirit and scope of the present invention. The invention is not limited in its application to the details of any particular formulation shown, since the invention is capable of other embodiments. The following examples are provided for illustrative purposes and do not and should not be understood to limit the claims appended hereto. The terminology used herein is for the purpose of description and not of limitation.

Description of the Test Methods

The beneficial effects of the combination therapy according to the invention can e.g. be shown in a clinical test protocol and in a pharmacological test model in the rat.

Clinical Test Protocol

A randomized, placebo-controlled, parallel group, multi-center, single dose study of oral daglutril (vide supra) during 12-hour right heart catheterization in human subjects with congestive heart failure (=CHF) was performed. Each subject received one dose of daglutril or placebo. The study consisted of three visits (or study days when in-subjects were included). Ambulatory subjects were in hospital for two nights and one day.

Criteria for evaluating efficacy were systemic vascular resistance (=SVR), pulmonary capillary wedge pressure (=PCWP), cardiac output (=CO), heart rate (=HR), pulmonary and systemic systolic, diastolic and mean pressures; pulmonary vascular resistance (=PVR); stroke volume index (=SVI); cardiac index (=CI); transpulmonary gradient and neurohormones.

The primary efficacy parameter was the maximum decrease from baseline over 6 hours for SVR and was compared between treatment groups using analysis of covariance, with the baseline value as covariate and center and NYHA classification as factors. Testing was carried out one-sided at an overall significance level of $\alpha=0.05$. Adjustment for the multiple comparisons was controlled by applying Dunnett's procedure. In addition, the existence of a dose-response relationship for daglutril was evaluated by investigating linear, quadratic and cubic contrasts. The secondary efficacy parameter was the maximum change from baseline over 6 hours for PCWP and was analyzed in the same way as the primary variable. The maximum decrease from baseline over 12 hours, the change from for each individual time point and the adjusted area under the curve (=AUC) over 6 and 12 hours were analyzed for SVR and PCWP, using similar statistical methodology as for the main parameter of interest. All other tertiary efficacy parameters were analyzed using the same statistical methodology as for the primary efficacy parameter but at a two-sided 5% level of significance.

Criteria for evaluating safety were laboratory variables; electrocardiogram (=ECG); physical examinations; vital signs and adverse events (=AEs).

Criteria for inclusion comprised male or female (without childbearing potential) subjects, aged $\geq 18$ to $\leq 85$ years, with a history of chronic, symptomatic, mild to severe (NYHA Class II-IV) CHF for at least three months, with documented systolic dysfunction (left ventricular ejection fraction (=LVEF)$\leq 35\%$ by echocardiography) receiving a stable dose of their individually optimized medication regimen for at least one week prior to study enrollment.

(96) Subjects were screened and (75) were randomized and analyzed, (18) subjects in the 200 mg daglutril group, (20) subjects in the 400 mg daglutril group, (19) subjects in the 800 mg daglutril group and (18) subjects in the placebo group. In a subgroup analysis, the 75 randomized subjects in the study were divided into subgroups, namely placebo or daglutril treatment with criterion present or absent. As criterion was taken whether concomitant medication of a HMG CoA reductase inhibitor was taken prior to and continued after randomization. In the placebo group, 6 patients took a HMG CoA reductase inhibitor (2 atorvastatin, 1 atorvastatin calcium, 3 simvastatin). In the 200 mg daglutril group, 6 patients took a HMG CoA reductase inhibitor (1 atorvastatin calcium, 1 pravastatin, 4 simvastatin). In the 400 mg daglutril group, 11 patients took a HMG CoA reductase inhibitor (3 atorvastatin, 1 atorvastatin calcium, 1 pravastatin sodium, 6 simvastatin). In the 800 mg daglutril group, 6 patients took a HMG CoA reductase inhibitor (2 atorvastatin, 1 atorvastatin calcium, 3 simvastatin).

Summary statistics of the average over the first 6 hours (0.5, 6 hours; only computed if no time points have missing data) (mean, Standard Deviation (=SD), n) are given. Both, for the criterion present and absent subgroups, the placebo corrected mean values and summary statistics (mean change, standard error of change (=SE) and standardized mean change (=mean/SE) are given.

In this test model, administration of daglutril in addition to a concomitant medication with an HMG CoA reductase inhibitor (namely atorvastatin, atorvastatin calcium, pravastatin, pravastatin sodium or simvastatin) prior to and after randomisation, respectively, showed the results on placebo corrected mean change of mean pulmonary artery pressure (=MPAP; 0.5-6 hrs) as given in table 1 below:

TABLE 1

Pharmacological results of coadministration of daglutril and HMG CoA reductase inhibitor on MPAP

| | daglutril and no HMG CoA reductase inhibitor [mm Hg] (SE) | daglutril with HMG CoA reductase inhibitor [mm Hg] (SE) |
| --- | --- | --- |
| Placebo corrected mean change of MPAP (average 0.5-6 hrs) | −2.26 (1.05) | −5.65 (2.12) |

The test results show that administration of a HMG CoA reductase inhibitor in addition to a dually acting compound capable of inhibiting NEP and the endogenous endothelin producing system, namely daglutril, resulted in an additional and beneficial decrease in pulmonary blood pressure measured as MPAP, when compared to the administration of a dually acting compound capable of inhibiting NEP and the endogenous endothelin producing system as a monotherapy. The beneficial influence on pulmonary blood pressure of a dually acting compound capable of inhibiting NEP and the endogenous endothelin producing system, namely daglutril, in addition to an HMG CoA reductase inhibitor was relevantly more marked than the influence that resulted from administration of a dually acting compound of inhibiting NEP and the endogenous endothelin producing system, namely daglutril, alone.

Animal Test Model

Male spontaneously hypertensive rats (=SHR; insulin resistant strain from Charles River; aged 6 months) were equipped with telemetry transmitters for continuous monitoring of blood pressure and heart rate (TA11PA-C40, DSI, USA). Telemetry transmitters for continuous monitoring of blood pressure, heart rate and locomotor activity (TA11PA-C40, Data Sciences, USA) were implanted intraabdominally under inhalative halothane anesthesia. A midline abdominal incision was made, and the abdominal aorta was visualized by removal of retroperitoneal fat and connective tissue. A ligature was placed caudal of the renal arteries, the aorta was punctured with a 22G needle, and the catheter was advanced into the aorta. The entry point was sealed with tissue adhesive (Vetbond™, 3M, USA), the ligature was removed, and the abdominal incision was closed. Measurements of aortic pressure were taken every 5 minutes (=min) for 4 seconds (=s) each at a sampling rate of 500 Hz, and were corrected for the corresponding ambient pressure (ambient pressure monitor, C11PR, Data Sciences, USA).

In a first experiment, after 3 days of monitoring under baseline (untreated) conditions, animals received daglutril via the drinking water. The intended daily dose was 100 mg/kg/day of daglutril. The concentration in drinking water was adjusted once per week, resulting in an average drug intake of 98 mg/kg/day.

In a second experiment, rats were divided into two groups receiving the HMG CoA reductase inhibitor simvastatin or a combination of simvastatin+daglutril. Compounds were administered via the drinking water, and daily drug intake was measured by weighing the water bottles thrice weekly. Intended daily doses were 40 mg/kg/day of simvastatin plus, in the combination group, 100 mg/kg/day of daglutril.

Concentrations of simvastatin and daglutril in the drinking water were adjusted once per week, in order to ensure the intended daily intake of 40 and 100 mg/kg, respectively. The average daily water intake amounted to 33 and 36 ml/kg in the simvastatin and simvastatin+daglutril group, respectively, resulting in the uptake of 36 mg/kg/day of simvastatin in the simvastatin group, and 37 mg/kg/day of simvastatin and 93 mg/kg/day of daglutril in the combination group.

The blood pressure, heart rate and activity values sampled in 5 min intervals by the Dataquest® system were used for calculation of individual 24 hours (=h) means. These 24 h means were exported to Excel®, and group mean values of systolic (SBP), diastolic blood pressure (DBP), heart rate (HR), and locomotor activity (ACT) were calculated daily. For the statistical analysis, the effects of simvastatin and simvastatin+daglutril were calculated by subtracting the baseline value (pre) measured on the last day prior to compound application (day 3) from that value measured on day 23 (i.e. on the penultimate day of the treatment period) for each animal. The statistical comparison was done by using univariate ANOVA at an error level of $P<0.05$.

In this test model, administration of daglutril in combination with an HMG CoA reductase inhibitor (simvastatin) and compared to administration of simvastatin only and daglutril only, showed the results as given in table 2 below:

TABLE 2

Effects of coadministration of daglutril and HMG CoA reductase inhibitor (simvastatin) on cardiovascular parameters in the spontaneously hypertensive rat

| Parameter | Simvastatin only | | Daglutril only | | Simvastatin + daglutril | | Statistics |
|---|---|---|---|---|---|---|---|
| | Mean | SEM | Mean | SEM | Mean | SEM | ANOVA |
| DBP [mmHg] | 4.7 | 0.5 | 2.0* | 0.5 | −3.2*# | 3.7 | P < 0.01 |
| SBP [mmHg] | 4.2 | 2.4 | −0.3* | 0.9 | −9.5*# | 1.6 | P < 0.001 |
| HR [1/min] | −4.2 | −6.2 | −6.0 | 2.1 | −5.5 | 8.0 | n.s. | n = 4-5 animals per group;
SEM = Standard Error of the Mean;
*P < 0.05 versus simvastatin only;
P < 0.05 combination versus daglutril only; two-tailed Student's test;
n.s. = not significant Simvastatin only resulted in a slight increase in blood pressure, daglutril only had no effect on blood pressure, while the combination group simvastatin+daglutril showed a clear decrease in blood pressure. The difference in blood pressure effects between the groups was statistically significant (ANOVA, at least P<0.01).

In a further study performed with a new batch of SHR equipped with telemetry-transmitters as described above, the animals were divided into two groups receiving the HMG CoA reductase inhibitor atorvastatin or a combination of atorvastatin+daglutril. Compounds were mixed into the food, and the daily drug intake was measured by weighing the unconsumed food four times weekly. Intended daily doses were 40 mg/kg/day of atorvastatin and in addition, in the combination group, 100 mg/kg/day of daglutril.

Concentrations of atorvastatin and daglutril in the food were adjusted once per week. The average daily food intake was 60, and 58 g/kg in the atrovastatin, and atorvastatin+daglutril group, respectively, resulting in the uptake of 32.6 mg/kg/day of atorvastatin in the atrovastatin group, and 31.3 mg/kg/day of atorvastatin and 78.3 mg/kg/day of daglutril in the combination group.

The blood pressure, heart rate and activity values were sampled, and calculations were made as described in the above studies with simvastatin. For the statistical analysis, the effects of atorvastatin and atorvastatin+daglutril were calculated by subtracting the baseline value (pre) measured on the last day prior to the start of treatment (day 3) from that measured on day 25 (i.e. on the penultimate day of the treatment period) for each animal. The statistical comparison was done by using a two-sided unpaired Student's t-test.

In this test model, administration of daglutril in combination with an HMG CoA reductase inhibitor (atorvastatin) and compared to administration of atorvastatin only and daglutril only (see above), showed the results as given in table 3 below:

TABLE 3

Effects of coadministration of daglutril and HMG CoA reductase inhibitor (atorvastatin) on cardiovascular parameters in the spontaneously hypertensive rat

| Parameter | Atorvastatin only | | Atorvastatin + daglutril | |
|---|---|---|---|---|
| | Mean | SEM | Mean | SEM |
| DBP [mmHg] | 3.2 | 1.9 | −1.4* | 1.1 |
| SBP [mmHg] | 3.5 | 2.2 | −3.1** | 0.8 |
| HR [1/min] | −25.3 | 3.0 | −21.6 | 2.3 | n = 6 animals per group;
*P < 0.05,
**P < 0.01 versus atorvastatin only (two-tailed Student's t-test)

As with simvastatin, the group treated with atorvastatin alone showed an increase in blood pressure (both SBP and DBP), whereas in the combination group, a decrease in blood pressure was observed, the difference between the values for atorvastatin alone and atorvastatin+daglutril being statistically significant.

The dosage of the active agents can depend on a variety of factors, such as mode of administration, species, age and/or individual condition. Suitable dosages for the active agents of the pharmaceutical combination according to the present invention are therapeutically effective dosages, for example those which are commercially available. Normally, in the case of oral administration, an approximate daily dose of from about 4 mg to about 600 mg is to be estimated for each of the active agents e.g. for a patient of approximately 75 kg in weight. For example, a pharmaceutical composition according to the invention may preferably comprise daglutril as dually acting compound capable of inhibiting NEP and the endogenous endothelin producing system in the range of 5-600 mg. The daily dose range of HMG CoA reductase inhibitors which can be used the pharmaceutical compositions according to the invention may vary depending on i.a. the substance used and may be (each calculated for the pure active substance, not the salt or solvate thereof), e.g., 10-80 mg for atorvastatin, 40-80 mg for fluvastatin, 20-80 mg for lovastatin, 10-40 mg for pravastatin or 10-80 mg for simvastatin. The administration of the pharmaceutical composition may occur up to three times a day. Once daily administration forms are preferred.

EXAMPLE I

Capsules containing daglutril and simvastatin:

Capsules with the following composition per capsule were produced:

| | |
|---|---|
| Daglutril calcium salt | 200 mg |
| Simvastatin | 50 mg |

-continued

| | |
|---|---|
| Corn starch | 50 mg |
| Lactose | 80 mg |
| Ethyl acetate | q.s. |

The active agents, the corn starch and the lactose were processed into a homogeneous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:

| | |
|---|---|
| Talcum | 5 mg |
| Magnesium stearate | 5 mg |
| Corn starch | 10 mg | and then poured into 400 mg capsules (=capsule size 0).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereto.

What is claimed is:

1. A pharmaceutical composition comprising
   a) a dual acting compound which acts as a neutral endopeptidase-inhibitor and as an inhibitor of the endogenous endothelin producing system and is selected from the group consisting of daglutril and physiologically compatible salts thereof in an amount of 5-600 mg, and
   b) at least one HMG CoA reductase inhibitor selected from the group consisting of atorvastatin in an amount of 10-80 mg, pravastatin in an amount of 10-40 mg, and simvastatin in an amount of 10-80 mg.

2. A pharmaceutical composition according to claim 1, further comprising at least one pharmaceutically acceptable auxiliary substance or carrier.

3. A pharmaceutical composition according to claim 1 which is configured for oral administration.

4. A pharmaceutical composition according to claim 3 wherein the active agents are present in one or more dosage forms selected from the group consisting of tablets, coated tablets, capsules, syrups, elixirs or suspensions.

5. A pharmaceutical composition according to claim 1, wherein the HMG CoA reductase inhibitor is present in a unit single dosage form physically segregated from the dual acting neutral endopeptidase-inhibitor and inhibitor of the endogenous endothelin producing system.

6. A pharmaceutical composition according to claim 1, wherein the HMG CoA reductase inhibitor is atorvastatin or simvastatin.

7. A method of treating or ameliorating a hypertension in a mammal comprising administering to a subject in need thereof a combination of a dual acting compound which acts as a neutral endopeptidase inhibitor and as an inhibitor of the endogenous endothelin producing system and is selected from the group consisting of daglutril and physiologically compatible salts thereof in an amount of 5-600 mg/day and at least one HMG CoA reductase inhibitor selected from the group consisting of atorvastatin in an amount of 10-80 mg/day, pravastatin in an amount of 10-40 mg/day, and simvastatin in an amount of 10-80 mg/day.

8. A method according to claim 7, wherein the dual acting compound; and the at least one HMG CoA reductase inhibitor are administered simultaneously, separately or in physical combination.

9. A method according to claim 7, wherein a fixed combination of the dual acting compound; and the at least one HMG CoA reductase inhibitor is administered.

10. A method according to claim 9, wherein the fixed combination comprises daglutril and simvastatin or daglutril and atorvastatin.

11. A kit comprising:
    in a first separate container,
       a pharmaceutical dosage form comprising a dually acting compound capable of inhibiting neutral endopeptidase and the endogenous endothelin producing system and selected from the group consisting of daglutril and physiologically compatible salts thereof in an amount of 5-600 mg, and
    in a second separate container,
       a pharmaceutical dosage form comprising at least one HMG CoA reductase inhibitor selected from the group consisting of atorvastatin in an amount of 10-80 mg, pravastatin in an amount of 10-40 mg, and simvastatin in an amount of 10-80 mg,
    the pharmaceutical dosage forms being suitable for simultaneous, separate or step-wise administration,
       wherein said first separate container and said second separate container are in a single package for use in combination.

12. A kit according to claim 11, wherein
    the dually acting compound capable of inhibiting neutral endopeptidase and the endogenous endothelin producing system is daglutril, and
    the at least one HMG CoA reductase inhibitor is simvastatin or atorvastatin.

13. A kit according to claim 11, further comprising a leaflet indicating that the at least one neutral endopeptidase inhibitor and the at least one inhibitor of the endogenous endothelin producing system or the dually acting compound capable of inhibiting neutral endopeptidase and the endogenous endothelin producing system may be administerd administered in combination with the at least one HMG CoA reductase inhibitor simultaneously, separately or in physical combination.

* * * * *